(12) United States Patent
Garay et al.

(10) Patent No.: US 8,916,209 B2
(45) Date of Patent: *Dec. 23, 2014

(54) EXTRACTS OF PHYLLANTHUS NIRURI

(75) Inventors: Michelle Garay, Pittstown, NJ (US);
Simarna Kaur, Green Brook, NJ (US);
Michael Southall, Lawrenceville, NJ (US); Ping Wen, Belle Mead, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 351 days.

This patent is subject to a terminal disclaimer.

(21) Appl. No.: 12/572,373

(22) Filed: Oct. 2, 2009

(65) Prior Publication Data

US 2011/0081304 A1 Apr. 7, 2011

(51) Int. Cl.
*A61K 36/00* (2006.01)
*A61K 36/47* (2006.01)
*A61K 8/97* (2006.01)
*A61Q 19/02* (2006.01)
*A61Q 19/08* (2006.01)

(52) U.S. Cl.
CPC . *A61K 36/47* (2013.01); *A61K 8/97* (2013.01); *A61Q 19/02* (2013.01); *A61Q 19/08* (2013.01)
USPC .......................................... 424/725; 424/779

(58) Field of Classification Search
None
See application file for complete search history.

(56) References Cited

U.S. PATENT DOCUMENTS

| | | | |
|---|---|---|---|
| 4,337,370 A | 6/1982 | Takisawa et al. | |
| 4,489,057 A | 12/1984 | Welters et al. | |
| 5,776,439 A | 7/1998 | Raspanti et al. | |
| 6,410,062 B1 | 6/2002 | Callaghan et al. | |
| 2005/0085454 A1 | 4/2005 | Ghosal | |
| 2007/0166255 A1 | 7/2007 | Gupta | |
| 2007/0196523 A1 | 8/2007 | Koganov | |
| 2008/0031833 A1 | 2/2008 | Oblong et al. | |
| 2010/0322883 A1* | 12/2010 | Gohier et al. | 424/63 |
| 2011/0081308 A1 | 4/2011 | Kaur et al. | |
| 2011/0081432 A1 | 4/2011 | Kaur et al. | |

FOREIGN PATENT DOCUMENTS

| | | |
|---|---|---|
| CN | 101332265 A | 12/2008 |
| EP | 1352640 | 10/2003 |
| JP | 8012566 A | 1/1996 |
| JP | 8176004 A | 7/1996 |
| JP | 1966176004 A | 7/1996 |
| JP | 9087136 A | 3/1997 |
| JP | 1997087136 A | 3/1997 |
| JP | 2002308750 A * | 10/2002 |
| JP | 2005008572 A * | 1/2005 |
| WO | WO 2009/067095 | 5/2009 |

OTHER PUBLICATIONS

Colipa Guideline: Guideline for the Colorimetric Determination of Skin Colour Typing and Prediction of the Minimal Erythemal Dose (MED) Without UV Exposure, published in 2007, p. 1-11.
Martin et al., "Parthenolide-depleted Feverfew (*Tanacetum parthenium*) protects skin from UV irradiation and external aggression", Arch Dermatol Res. (2008) 300:69-80.
www.rain-tree.com, "Database File for: Chanca Piedra (*Phyllanthus niruri*)" reprinted from Taylor, "The Healing Power of Rainforest Herbs", (2005).
Chaudhuri RK, "Emblica Cascading Antioxidant: A Novel Natural Skin Care Ingredient", Skin Pharmacol Appl Skin Physiol. Sep.-Oct. 2002; 15(5):374-80.
Barros, M.E. et al., "Effects of an aqueous extract from *Phyllantus niruri* on calcium oxalate crystallization in vitro", Urol Res. Feb. 2003, 30(6):374-9.
Ogata, T. et al., "HIV-1 reverse transcriptase inhibitor from *Phyllantus niruri*", AIDS Res Hum Retroviruses Nov. 1992; 8(11): 1937-44.
Qian-Cutrone, J. et al., "Niruriside, a new HIV REV/RRE binding inhibitor from *Phyllanthus niruri*", J Nat Prod Feb. 1996; 59(2):196-9.
Kiemer, A.K., et al., "*Phyllanthus amarus* has anti-inflammatory potential by inhibition of iNOS, COX-2 and cytokines via the NF-kappaB pathway", J Hepatol. Mar. 2003; 38(3):289-97.
Bagalkotkar, G., "Phytochemicals from *Phyllanthus niruri* Linn. and their pharmacological properties: a review", J Pharm Pharmacol. 2006; 58(12):1559-70.
PCT International Search Report for International Application No. PCT/US2010/051089 dated Mar. 14, 2011.
Xiuqing, Zheng, "In vitro antibacterial activity of aqueous extract of a water extract of *Phyllanthus niruri*", Modern Animal Husbandry, No. 11, 2008, p. 48-49, Machine Translation.
Xiuqing, Zheng, "Antioxidant activity and Liver-protect activity in vitro from extracts of *Phyllanthus urinaria* L.", Husbandry and Veterinary in Fujian, vol. 30, No. 6, 2008, Machine Translation.
Kassuya et al., "Antiinflammatory and antiallodynic actions of the lignan niranthin isolated from *Phyllanthus amarus*," European Journal of Pharmacology, Elsevier BV, NL, vol. 546, No. 1-3, Sep. 28, 2006, pp. 182-188, XP005646245.
Kassuya et al., "Anti-Inflammatory Properties of Extracts, Fractions and Lignans Isolated from *Phyllanthus amarus*," Planta Medica, Thieme Verlag, DE, vol. 71, No. 8, Aug. 1, 2005, pp. 721-726, XP009145102.
Database WPI, Week 199612, Thomson Scientific, London, GB; AN 1996-112627, XP002625249, Jan. 16, 1996.
Database WPI, Week 199723, Thomson Scientific, London, GB; AN 1997-255417, XP002625250, Mar. 31, 1997.
Database WPI, Week 199637, Thomson Scientific, London, GB; AN 1996-368117, XP002625251, Jul. 9, 1997.

\* cited by examiner

*Primary Examiner* — Chris R Tate
*Assistant Examiner* — Deborah Davis
(74) *Attorney, Agent, or Firm* — Sharon E. Hayner

(57) ABSTRACT

A method of making a low molecular weight fraction of *Phyllanthus niruri* is provided. Such low molecular weight fraction is particularly useful for treating the signs of skin aging.

1 Claim, No Drawings

EXTRACTS OF *PHYLLANTHUS NIRURI*

FIELD OF THE INVENTION

The present invention relates to compositions comprising, as well as methods of making and using, extracts of *Phyllanthus niruri*. The compositions are useful for example for improving the appearance of aged skin.

BACKGROUND OF THE INVENTION

Aging of the skin can adversely affect elasticity and strength of the skin through changes in the two main constituents of the dermal extracellular matrix, the fibrous proteins collagen and elastin. For example, elastin is a large fibrous protein formed by the crosslinking of elastin precursor protein molecules (e.g., tropoelastin) into spiral filaments. The spiral filaments consist of peptidic chains that are capable of extending and then resuming their original shape.

Compositions comprising *Phyllanthus niruri* to treat the skin are known in the art. However, the inventors have recognized that not all extracts of *Phyllanthus niruri* perform equivalently in promoting tropoelastin and collagen formation. The inventors have surprisingly found that water-extractable, low molecular weight fractions of *Phyllanthus niruri* have significantly better activity than other extracts of *Phyllanthus niruri* for inhibiting collagenase, promoting tropoelastin, and promoting collagen formation.

SUMMARY OF THE INVENTION

The invention relates to a composition consisting essentially of a low molecular weight fraction of *Phyllanthus niruri* substantially free of molecular species having a molecular weight of greater than about 100,000 daltons.

The invention also relates to a topical formulation comprising a cosmetically acceptable topical carrier and a composition consisting essentially of a low molecular weight fraction of *Phyllanthus niruri* substantially free of molecular species having a molecular weight of greater than about 100,000 daltons, as well as a method of treating a sign of skin aging by topically applying such topical formulation to the skin.

The invention further relates to a method of making a low molecular weight fraction of *Phyllanthus niruri*, said method comprising: contacting *Phyllanthus niruri* with a solvent comprising water for a time period sufficient to form a water extract of *Phyllanthus niruri*; and isolating a low molecular weight fraction from said water extract of *Phyllanthus niruri*.

Other features and advantages of the present invention will be apparent from the detailed description of the invention and from the claims.

DETAILED DESCRIPTION OF PREFERRED EMBODIMENTS

Unless defined otherwise, all technical and scientific terms used herein have the same meaning as commonly understood by one of ordinary skill in the art to which the invention belongs. Also, all publications, patent applications, patents, and other references mentioned herein are incorporated by reference. Unless otherwise indicated, a percentage or concentration refers to a percentage or concentration by weight (i.e., % (W/W). Unless stated otherwise, all ranges are inclusive of the endpoints, e.g., "from 4 to 9" includes the endpoints 4 and 9.

As used herein, "signs of skin aging" includes the presence of lines and wrinkles, loss of elasticity, uneven skin, blotchiness, and age spots.

As used herein, "treating" refers to mitigating, reducing, preventing, improving, or eliminating the presence or appearance of a condition or disease.

As used herein, "wrinkle" includes fine lines, fine wrinkles, or coarse wrinkles. Examples of wrinkles include, but are not limited to, fine lines around the eyes (e.g., "crow's feet"), forehead and cheeks, frown-lines, and laugh-lines around the mouth.

As used herein, "loss of elasticity" includes loss of elasticity or structural integrity of the skin or tissue, including but not limited to sagging, lax and loose tissue. The loss of elasticity or tissue structure integrity may be a result of a number of factors, including but not limited to disease, aging, hormonal changes, mechanical trauma, environmental damage, or the result of the application of products, such as cosmetics or pharmaceuticals, to the tissue.

As used herein, "uneven skin" means a condition of the skin associated with diffuse or mottled pigmentation, which may be classified as hyperpigmentation, such as post-inflammatory hyperpigmentation.

As used herein, "blotchiness" means a condition of the skin associated with redness or erythema.

As used herein, "age spots" means a condition of the skin associated with discrete pigmentation, e.g., small areas of darker pigmentation that may develop on the face as well as the hands.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein, "cosmetically effective amount" means an amount of a physiologically active compound or composition sufficient for treating one or more signs of skin aging, but low enough to avoid serious side effects. The cosmetically effective amount of the compound or composition will vary with the particular condition being treated, the age and physical condition of the user, the severity of the condition being treated/prevented, the duration of the treatment, the nature of other treatments, the specific compound or product/composition employed, the particular cosmetically-acceptable carrier utilized, and like factors.

It is believed that one skilled in the art can, based upon the description herein, utilize the present invention to its fullest extent. The following specific embodiments are to be construed as merely illustrative, and not limitative of the remainder of the disclosure in any way whatsoever.

*Phyllanthus niruri* may be harvested and used as the whole plant, or optionally one or more parts of the plant (e.g., flower, seed, root, rhizome, stem, fruit and/or leaf of the plant) may be used. The *Phyllanthus niruri* plant or parts thereof may be finely divided, such as by grinding or milling, to a powder. A suitable milled form of *Phyllanthus niruri* is commercially available from Raintree Nutrition, Inc., of Carson City, Nevada.

According to a first step of the method of the invention, *Phyllanthus niruri* (optionally prepared as discussed above) is contacted with a solvent comprising water for a time period sufficient to form a water extract of the *Phyllanthus niruri*. The solvent comprises water, preferably at least about 50% water, more preferably at least about 75% water, and most preferably at least about 90% water.

In one embodiment, the solvent comprises less than about 10% of organic solvents (e.g., ethanol, methanol, and the like). In a preferred embodiment, the solvent includes less than about 5% of organic solvents. In a further preferred embodiment, the solvent includes less than about 1% of organic solvents. In yet another preferred embodiment, the solvent includes no organic solvent. If organic solvent is included in the solvent, refluxing the resulting liquid phase in a temperature range from 60 to 100° C. may be required to remove the organic solvent.

Accordingly, in certain embodiments of the invention, the molecular species in the water extract of *Phyllanthus niruri* are water extractable. As used herein, "water extractable" means capable of being extracted by contacting with a solvent that includes at least about 50% water, more preferably at least about 75% water, and most preferably at least about 90% water.

The ratio of the mass of *Phyllanthus niruri* to solvent may be varied. In one embodiment the ratio of the mass of *Phyllanthus niruri* to solvent is from about 1:2 to about 1:50, preferably from about 1:3 to about 1:20, even more preferably from about 1:4 to about 1:12.

To enhance extraction, the *Phyllanthus niruri* may be sonicated in the solvent. Alternatively, or in addition, the solvent may be heated, such as to a temperature between about 30° C. and about 70° C., preferably from about 40° C. to about 65° C., more preferably from about 40° C. to about 65° C.

The *Phyllanthus niruri* and the solvent are preferably contacted for a time period of at least about 5 minutes, preferably from about 10 minutes to about 6 hours, more preferably from about 10 minutes to about 60 minutes, most preferably about 30 minutes.

The water extract is desirably separated by filtration using conventional filtration techniques, such as through a Buchner funnel using a Whatman filter paper. The resulting water extract of *Phyllanthus niruri* is then available for additional processing as follows.

According to a second step of the method of the invention, a low molecular weight fraction of the water extract of *Phyllanthus niruri* is then isolated. A suitable means for isolating the low molecular weight fraction is by gel filtration, i.e., gel permeation chromatography (GPC) employing a membrane that will selectively pass only those molecular species above or below a particular molecular weight cutoff.

As is well understood by those skilled in the art, a GPC column is first packed with a non-ionic crosslinked polymer resin. The resin is thoroughly washed, such as with the following liquids, in sequence: 1 liter of water, 1 liter of water-methanol, and 1 liter of methanol, followed by conditioning with water. The water extract of *Phyllanthus niruri* is the passed through for example a 100 kD (100,000 dalton) membrane using a Spectrum MiniKros to concentrate and separate molecules having molecular weights less than 100,000 dalton. The portion that passes through the membrane is isolated as the low molecular weight fraction of *Phyllanthus niruri*. The remaining portion of the water extract may optionally and preferably be discarded.

In this manner, a composition is made consisting essentially of a low molecular weight fraction of *Phyllanthus niruri* that is substantially free of molecular species having a molecular weight of greater than about 100,000 daltons. As used herein, "substantially free of molecular species having a molecular weight of greater than about 100,000 daltons" means such composition contains less than about 10% by weight, preferably less than about 5% by weight, more preferably less than about 2% by weight, even more preferably less than about 1% by weight, even more preferably less than about 0.5% by weight, and even more preferably less than about 0.1% by weight of molecular species having molecular weights greater than about 100,000 daltons. As one skilled in the art will readily appreciate, the concentration of molecular species having molecular weights greater than about 100,000 daltons in the low molecular weight fraction of *Phyllanthus niruri* may be adjusted by, for example, adjusting the cutoff molecular weights allowed through the membrane of the GPC.

The solvent (e.g., water) may or may not be dried off or evaporated. It should be noted that the percentages of molecular species having particular molecular weight ranges described herein are calculated exclusive of any residual solvent. In a preferred embodiment, the method of the invention further includes at least partially (or completely) removing remaining solvent in the low molecular weight fraction, such as by freeze drying.

Topical Formulations

The composition consisting essentially of a low molecular weight fraction of *Phyllanthus niruri* may be combined with one or more cosmetically acceptable topical carriers to form a topical formulation suitable for use on skin.

As used herein, "cosmetically acceptable" means suitable for use in contact with (human) tissues (e.g., the skin) without undue toxicity, incompatibility, instability, irritation, allergic response, and the like, commensurate with a reasonable benefit/risk ratio.

Suitable topical carriers include, but are not limited to, water, ethanol, isopropanol, 1,2-propanediol, glycerin, benzyl alcohol, dimethylisosorbide, triacetin, glycol ethers, propylene glycol, polyethylene glycol (PEG), and combinations thereof. Particularly preferred carriers include PEG having an average molecular weight between about 200 and about 400, castor oil, triacetin, dimethylisosorbide, ethanol, and water, and combinations thereof.

Various compounds may be added to the topical formulation to alter osmolarity and/or pH to acceptable levels. These include, but are not limited to, mannitol, sucrose, calcium chloride, sodium chloride, sodium phosphate monobasic, sodium phosphate dibasic, sodium hydroxide, and hydrochloric acid.

The topical formulations may be made into a wide variety of cosmetic articles that include but are not limited to lotions, creams, gels, sticks, sprays, ointments, cleansing liquid washes and solid bars, shampoos and hair conditioners, pastes, foams, powders, mousses, shaving creams, wipes, strips, patches, electrically-powered patches, wound dressing and adhesive bandages, hydrogels, film-forming products, facial and skin masks, make-up such as foundations, eye liners, and eye shadows, and the like.

These product types may contain several types of cosmetically acceptable topical carriers including, but not limited to solutions, suspensions, emulsions such as microemulsions and nanoemulsions, gels, solids and liposomes. Other carriers can be formulated by those of ordinary skill in the art. In order to facilitate the formulation of a suitable carrier, one may include any of various functional ingredients. For example, one may include any of a number of emollients, humectants, pH adjusters, sequesterants, emulsifiers, wetting agents, thickeners, polymers, preservatives, colorants, fragrances, and other ingredients commonly used in personal care and cosmetic products. The pH chosen is not critical, but may be in a range, for example that is from about 4 to about 8, such as from about 5 to about 7.

The cosmetically acceptable topical carrier may constitute from about 50% to about 99.99%, by weight, of the topical formulation, more preferably from about 80% to about 95%, by weight, of the topical formulation. In a particularly preferred embodiment, the topical formulation includes at least about 25% by weight water, more preferably at least about 50% by weight water.

In one embodiment, the topical formulation may further contain one or more additional cosmetically active agent(s) as well as the above-mentioned components. What is meant by a "cosmetically active agent" is a compound, which may be a synthetic compound or a compound extracted, isolated, purified or concentrated from a natural source, or a natural extract containing a mixture of compounds, that has a cosmetic or therapeutic effect on the tissue, including, but not limited to: anti-microbial agents such as anti-yeast, anti-fungal, and anti-bacterial agents, anti-inflammatory agents, anti-aging agents, depigmentaion agents, anti-parasite agents, antioxidants, keratolytic agents, nutrients, vitamins, minerals, energy enhancers, sunscreens and the like.

Examples of vitamins that may be constituents of the compositions of this invention include, but are not limited to, vitamin A, vitamin Bs such as vitamin B3, vitamin B5, vitamin B7 and vitamin B12, vitamin C, vitamin K, vitamin E such as alpha, gamma or delta-tocopherol, and their derivatives (such as salts and esters) and mixtures thereof.

Examples of antioxidants which may be utilized in the compositions and methods of this invention include, but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), different types of tocopherols (e.g., alpha-, gamma-, and delta-tocopherols and their esters such as acetate) and their mixtures, tocotrienols, and ubiquinone. Natural extracts containing antioxidants suitable for use in the compositions of this invention include, but are not limited to, extracts containing flavinoid, isoflavinoid, and their derivatives such as genistein and diadzein (e.g., such as soy and clover extracts, extracts containing resveratrol and the like. The one or more additional cosmetically active agent(s) may be present in any suitable concentration, such as, for example from about 0.1% to about 10% by weight.

Examples of anti-aging agents that which may be utilized include, but are not limited to, retinoids (e.g., retinol and retinyl palmitate) and amine compounds of formula I or formula II, shown below:

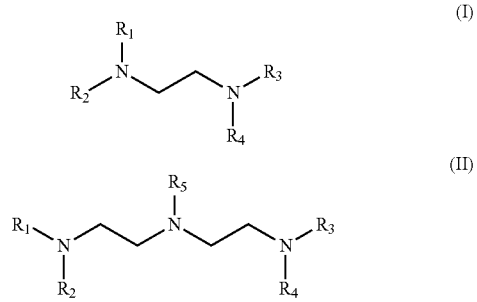

wherein $R_1$, $R_2$, $R_3$, $R_4$, and $R_5$ independently are selected from the group consisting of hydrogen, $C_1$-$C_6$ alkyl, and $C_1$-$C_6$ hydroxyalkyl; or a cosmetically-acceptable salt thereof.

Examples of preferred amine compounds of formula I include, but are not limited to, N,N,N',N'-tetrakis(2-hydroxypropyl)ethylenediamine (THPED), N,N,N',N'-tetrakis (2-hydroxyethyl)ethylene diamine (THEED), N,N,N', N'tetramethylethylene diamine (TEMED), enantiomers thereof, diastereoisomers thereof, and cosmetically-acceptable salts thereof.

Other examples of anti-aging actives include: copper containing peptides; vitamins such as vitamin E, vitamin C, vitamin B, and derivatives thereof such as vitamin E acetate, vitamin C palmitate, and the like; antioxidants including beta carotene, alpha hydroxy acids such as glycolic acid, citric acid, lactic acid, malic acid, mandelic acid, ascorbic acid, alpha-hydroxybutyric acid, pyruvic acid; beta hydroxy acids such as beta-hydroxybutyric acid, beta-phenyl-lactic acid, beta-phenylpyruvic acid; polyphenolics; botanical extracts such as green tea, soy products, milk thistle, algae, aloe, angelica, bitter orange, coffee, goldthread, grapefruit, hoellen, honeysuckle, Job's tears, lithospermum, mulberry, peony, puerarua, nice, safflower, and mixtures thereof.

Examples of suitable depigmentation agents include, but are not limited to soy products, retinoids such as retinol; Kojic acid and its derivatives such as, for example, kojic dipalmitate; hydroquinone and it derivatives such as arbutin; transexamic acid; vitamins such as niacin, vitamin C and its derivatives; azelaic acid; placertia; licorice; extracts such as chamomile and green tea, and mixtures thereof, with retinoids, Kojic acid, soy products, and hydroquinone being particularly suitable examples.

Examples of sunscreens include UV-A and UV-B absorbing sunscreens. UV-A absorbing sunscreens include tertrahydroxybenzophenones; dicarboxydihydroxybenzophenones and alkane ester or acid halide derivatives thereof; dihydroxy-, dicarboxy-, and hydroxycarboxydibenzoylmethanes and alkane ester or acid halide derivatives thereof; dihydroxy-, dicarboxy-, and hydroxycarboxystilbenes and alkane ester or acid halide derivatives thereof; bis(hydroxystyrenyl) benzenes; bis(carboxystyrenyl)benzenes and alkane ester or acid halide derivatives thereof; dihydroxy-, dicarboxy, and hydroxycarboxycarotenes and alkane ester or acid halide derivatives thereof; 2 cyano-3,3-diphenyl acrylic acid, 2-ethyl hexyl ester; and any suitably functionalized species capable of copolymerization within the polymer chain capable of absorbing ultraviolet light in the 320-400 nm range.

In one embodiment, the sunscreen is a UV-absorbing triazole and/or a UV-absorbing benzoylmethane, such as methylene bis-benzotriazolyl tetramethylbutylphenol (TINSORB M, Ciba Specialty Chemicals Corporation, Greensboro, N.C., USA). Other UV-absorbing dibenzoylmethanes include 2-(4-diethyl amino-2 hydroxybenzol)-benzoic acid hexylkester, commercially available as UVINUL A Plus from BASF of Parsippany, N.J.

UV-absorbing dibenzoylmethanes are disclosed in U.S. Pat. No. 4,489,057 and include, but are not limited to, 4-(1, 1-dimethylethyl)-4'-methoxydibenzoylmethane (avobenzone and sold as PARSOL 1789, Roche Vitamins and Fine Chemicals, Nutley, N.J., USA), 2-2-methyldibenzoylmethane, 4-methyl-dibenzoylmethane, 4-isopropyldibenzoylmethane, 4-tert-butyldibenzoylmethane, 4-tert-butyl-4'-methoxydibenzoylmethane, 2,4-dimethylbenzoylmethane, 2,5-dimethylbenzoylmethane, 4,4'-diisopropylbenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, and 2,6-dimethyl-4-tert-butyl-4'-methoxydibenzoylmethane.

Examples of suitable UV-B absorbing sunscreens include 4-aminobenzoic acid and alkane esters thereof; anthranilic acid and alkane esters thereof; salicylic acid and alkane esters thereof; hydroxycinnamic acid alkane esters thereof; dihydroxy-, dicarboxy-, and hydroxycarboxybenzophenones and alkane ester or acid halide derivatives thereof; dihydroxy-, dicarboxy-, and hydroxycarboxychalcones and alkane ester or acid halide derivatives thereof; dihydroxy-, dicarboxy-, and hydroxycarboxycoumarins and alkane ester or acid halide derivatives thereof; and other suitably functionalized species capable of copolymerization within the polymer chain.

Particularly suitable UV-B absorbing moieties include UV-absorbing benzophenones and UV-absorbing diphenylcyanoacrylate derivatives. Examples of benzophenone derivatives include those known in the art to provide protection of the skin from UV radiation, for example, such as taught by U.S. Pat. No. 5,776,439. Preferred compounds include 2-hydroxy-4-methoxybenzophenone (oxybenzone) and 2-2' dihyroxy-4-methoxybenzophenone ("dioxybenzone") and diethylamine hydroxybenzoyl hexyl benzoate ("hydroxybenzophenone"). Examples of diphenylcyanoacrylate derivatives include 2-ethylhexyl 2-cyano-3,3-diphenyl-2-propenoate (octocrylene).

While the sunscreens may be "organic sunscreens" (also known as UV filters), such as those described above that absorb radiation in the UV, in certain embodiments, the formulation may also include "physical" sunscreens, generally water insoluble particulate compounds that scatter UV radiation. Examples of such physical sunscreens include zinc oxide and titanium oxide.

In one embodiment the topical formulation comprises a sunscreen selected from the group consisting of phenylbenzimidazole sulfonic acid, methylene bis-benzotriazolyl tetramethylbutylphenol, ethylhexyl salicylate, octocrylene, benzophenone-3, ethylhexyl triazone, avobenzone, homosalate, bis-ethylhexyloxyphenol methoxyphenyl triazine, and mixtures thereof.

The low molecular weight fraction of *Phyllanthus niruri*, cosmetically acceptable topical carrier and optional additional cosmetically active agents may be combined in any proportion to form a topical formulation suitable for topical use. In one embodiment of the invention, the topical formulation comprises at least about 0.1% by weight of the low molecular weight fraction of *Phyllanthus niruri*. In certain embodiments, the topical formulation comprises at least about 0.5%, say about 0.75% to about 2.0% by weight, of the low molecular weight fraction of *Phyllanthus niruri*.

Topical formulations comprising compositions consisting essentially of the low molecular weight fraction of *Phyllanthus niruri* may be topically applied to mammalian skin that is in need of treatment for one or more signs of skin aging as described above. In one embodiment, the topical formulations are applied to skin in need of treatment for lines and wrinkles and/or loss of elasticity. The topical formulations may be applied to the skin in need of such treatment according to a suitable treatment regimen, e.g., every month, every week, every other day, every day, twice a day, or the like.

In certain embodiments, topical formulations of the present invention may also be useful for treating other need states associated with skin. For example, the topical formulations may be useful for treating post-inflammatory depigmentation/hyperpigmentation, for reducing pore size, acne treatment, and for scar mitigation. In certain other embodiments, the topical formulations may be applied simultaneously with or within several hours of a mechanical or physical exfoliant such as a microdermabrasion treatment, or with a chemical exfoliant or keratolytic agent such as salicylic acid. In certain other embodiments, the topical formulations are applied to mucosa or other tissue such as vaginal, oral, or ocular tissue. In certain other embodiments, the topical formulations are applied to mild wounds or post-surgical sites to facilitate healing, to insect bites, to poison ivy or similar skin conditions, or in general to mitigate itch. In certain other embodiments, the topical formulations are applied to mitigate skin irritations. Such irritations may be of external origin, i.e., caused by ingredients in skin care and cosmetic products such as retinoids and their derivatives, benzoyl peroxide, alpha-hydroxy acids and derivatives thereof, salicylic acid, surfactants, natural plant extracts, sunscreen actives, urea, and preservatives etc. Such irritations may be of other external origin such as the sun, wind, or shaving. Irritation may also be caused by diseases and conditions such as acne, rosacea, atopic dermatitis, and other disease states.

It is believed that one skilled in the art can, based upon the description herein, utilize the present invention to its fullest extent. The following specific embodiments are to be construed as merely illustrative, and not limitative of the remainder of the disclosure in any way whatsoever. The following non-limiting examples further illustrate the invention.

EXAMPLE I

Four different solvent extracts of *Phyllanthus niruri* were prepared. *Phyllanthus niruri* (Raintree Nutrition, Inc., Carson City, Nev.) was extracted separately in each of methanol, hexane, ethyl acetate, and water by sonicating for 30 min at 60° C. No molecular weight fractionation was performed on the solvent extracts, each of which was recovered by filtration though a Buchner funnel using a Whatman filter paper. Volatiles were evaporated by freeze drying.

EXAMPLE II

Enzyme activities of the solvent extracts of *Phyllanthus niruri* of Example I were evaluated for collagenase inhibition using the EnzChek Collagenase assay. The ability of each solvent extract to inhibit the activity of the collagenase Type IV enzyme from *Clostridium histolyticum* on the DQ elastin from pig skin (substrate) was fluorometrically assayed in a Microplate reader. The $IC_{50}$ values are indicated below in Table 1.

TABLE 1

| Extract | IC50 value for the Collagenase Enzyme |
| --- | --- |
| Methanol Extract Of *Phyllanthus niruri* | >500 ug/ml |
| Hexane Extract Of *Phyllanthus niruri* | 223.1 ug/ml |
| Ethyl acetate Extract Of *Phyllanthus niruri* | 334.6 ug/ml |
| Water Extract Of *Phyllanthus niruri* | 27.6 ug/ml |

The water extract of *Phyllanthus niruri* provided a substantially greater collagenase inhibition than the methanol, hexane, or ethyl acetate extracts.

EXAMPLE III 51.2 g of *Phyllanthus niruri* (Raintree Nutrition, Inc., Carson City, Nev.) was extracted with 320 mL of water by sonicating for 30 min at 60° C. The liquid phase was removed by filtration though a Buchner funnel using a Whatman filter paper.

A gel fractionation column was packed with 60 g of XAD-4 resin (non-ionic crosslinked polymer resin). The resin was thoroughly washed in sequence with water (1 L volume), water-methanol (50:50, 1 L), methanol (1 L) and conditioned with water prior to loading. The above prepared water extract was passed through a 100 kD membrane using Spectrum MiniKros (Spectrum Laboratories, Inc., Rancho Dominguez, Calif.) to concentrate and separate small molecules, yielding a low molecular weight fraction of the water extract.

A comparative water extract of *Phyllanthus niruri* was not fractionated (i.e., it contained both low molecular weight and high molecular weight species).

Volatiles were evaporated by freeze drying.

Enzyme activities of both water extracts were evaluated for collagenase enzyme activity. The IC50 values are indicated in Table 2 below.

TABLE 2

| Extract | IC50 value for the Collagenase Enzyme |
|---|---|
| *Phyllanthus niruri* Water Extract | 27.6 ug/ml |
| Low Molecular Weight fraction of *Phyllanthus niruri* Water Extract | 7.8 ug/ml |

These results demonstrate that the low molecular weight fraction of the *Phyllanthus niruri* water extract provides a substantially greater, i.e., more than three times greater, collagenase inhibition than *Phyllanthus niruri* water extract containing both high and low molecular weight molecular species.

EXAMPLE IV 51.2 g of *Phyllanthus niruri* (Raintree Nutrition, Inc., Carson City, Nev.) was extracted with 320 mL of water by sonicating for 30 min at 60° C. The liquid phase was removed by filtration though a Buchner funnel using a Whatman filter paper.

A gel fractionation column was packed with 60 g of XAD-4 resin (non-ionic crosslinked polymer resin). The resin was thoroughly washed in sequence with water (1 L volume), water-methanol (50:50, 1 L), methanol (1 L) and conditioned with water prior to loading. The above prepared water extract was passed through a 100 kD membrane using Spectrum MiniKros (Spectrum Laboratories, Inc., Rancho Dominguez, Calif.) to concentrate and separate small molecules, yielding 6.4 g of the low molecular weight fraction and 2.8 g of the high molecular weight fraction.

A tropoelastin promoter assay was conducted on different samples of water extracts of *Phyllanthus niruri* (i.e., the high molecular weight fraction and the low molecular weight fraction as prepared above, and a water extract containing all molecular weight species that had not been subjected to fractionation).

Specifically, rat cardiac myoblasts H9C2 cells were purchased from ATCC (Manassas, Va.). Cultures were maintained in Dulbecco's modified Eagle's medium (DMEM from Invitrogen Life Technologies, Carlsbad, Calif.) supplemented with 10% fetal bovine serum, 100 units/ml penicillin, and 50 ug/ml streptomycin (Invitrogen life technologies, Carlsbad, Calif.).

Cell cultures were transiently transfected with the elastin promoter-luciferase reporter construct (Elp2.2-a 2.2 kb Elastin promoter fragment from nt −2267 to nt +2), driving the firefly luciferase gene, which was obtained from Promega (Madison, Wis.). In all transfections, a construct with the thymidine kinase promoter and the Renilla luciferase reporter gene (pRL-TK, Promega, Madison, Wis.) was included as an internal control.

Cells grown in 48-well plates were transfected with 0.45 ug total DNA per well using Lipofectamine 2000 (Invitrogen life technologies, Carlsbad, Calif.). One day after transfection, cells were treated with the water extracts of *Phyllanthus niruri* (whole, high molecular weight fraction, or low molecular weight fraction) at multiple concentrations for approximately 24 hours before they were lysed for luciferase assays, using Dual-Luciferase Reporter System from Promega (Madison, Wis.), following manufacturer's protocol. The firefly luciferase activity was measured first (representing elastin promoter activity), followed by the renilla luciferase (internal control), using luminometer LMAX, from Molecular Devices (Sunnyvale, Calif.). The ratio of these two luciferase activities (RLU) was used to evaluate the activity of each sample.

Prior to subjecting to the tropoelastin promoter assay, each water extract was dissolved in DMSO-Water (50:50) at a stock concentration of 1.0 mg/mL, and was diluted into tissue culture media containing 2% serum from that stock.

The results are shown below in Table 3.

TABLE 3

| Sample | Concentration (on active basis) | Increase in Tropoelastin Promoter Activity Over Control |
|---|---|---|
| *Phyllanthus niruri* (whole) Water Extract, not fractionated | 0.1 ug/mL 0.025 ug/mL | 1.22 ± 0.19** 1.85 ± 0.54* |
| Water Extract, High Molecular Weight Fraction | 0.025 ug/mL | 1.97 ± 0.46** |
| Water Extract, Low Molecular Weight Fraction | 0.025 ug/mL | 2.35 ± 0.27* |
| Vehicle Control (DMSO) | 0.0025% | 1.00 ± 0.43 |

*= P < 0.05 using a Student's t-Test
**= P < 0.1 using a Student's t-Test

The low molecular weight fraction of the *Phyllanthus niruri* water extract resulted in a substantial increase tropoelastin promotion compared to the *Phyllanthus niruri* water extract containing both high and low molecular weight species. Tropoelastin promotion was 27% higher for the low molecular weight fraction (2.35) compared to the water extract containing all molecular weight species (1.85).

EXAMPLE V

A collagen promoter assay was conducted as follows on the samples of water extracts of *Phyllanthus niruri* described in Example III (i.e., a high molecular weight fraction, a low molecular weight fraction, and a water extract containing the full range of molecular weight species).

Rat cardiac myoblasts H9C2 cells were purchased from ATCC (Manassas, Va.). Cultures were maintained in Dulbecco's modified Eagle's medium (DMEM from Invitrogen Life Technologies, Carlsbad, Calif.) supplemented with 10% fetal bovine serum, 100 units/ml penicillin, and 50 ug/ml streptomycin (Invitrogen life technologies, Carlsbad, Calif.).

Cell cultures were transiently transfected with the Collagen1A promoter-luciferase reporter construct, driving the firefly luciferase gene, which was obtained from PREMAS Biotech Pvt. Ltd (Haryana, India). In all transfections, a construct with the thymidine kinase promoter and the Renilla luciferase reporter gene (pRL-TK, Promega, Madison, Wis.) was included as an internal control.

Cells grown in 48-well plates were transfected with 0.45 ug total DNA per well using Lipofectamine 2000 (Invitrogen life technologies, Carlsbad, Calif.). One day after transfection, cells were treated with *Phyllanthus niruri* (whole or high or low molecular weight fractions) at multiple concentrations for approximately 24 hours before they were lysed for luciferase assays, using Dual-Luciferase Reporter System from Promega (Madison, Wis.), following manufacturer's protocol. The firefly luciferase activity was measured first (representing collagen promoter activity), followed by the renilla luciferase (internal control), using luminometer LMAX, from Molecular Devices (Sunnyvale, Calif.). The ratio of these two luciferase activities (RLU) was used to evaluate the activity of each promoter.

Prior to subjecting to the collagen promoter assay, each water extract was dissolved in DMSO-Water (50:50) at a stock concentration of 1.0 mg/mL, and was diluted into tissue culture media containing 2% serum from that stock.

The results are shown below in Table 4.

TABLE 4

| Sample | Concentration (on active basis) | Increase in Collagen1A Promoter Activity Over Control |
|---|---|---|
| *Phyllanthus niruri* (whole) Water Extract | 0.5 ug/mL | 1.27 ± 0.29** |
| Water Extract | 0.5 ug/mL | 1.51 ± 0.12** |
| Water Extract, High Molecular Weight Fraction | 0.5 ug/mL | 1.55 ± 0.15** |
| Water Extract, Low Molecular Weight Fraction | 0.5 ug/mL | 2.03 ± 0.12* |
| Vehicle Control (DMSO) | 0.05% | 1.00 ± 0.13 |

*= $P < 0.05$ using a Student's t-Test
**= $P < 0.1$ using a Student's t-Test

The low molecular weight fraction of the *Phyllanthus niruri* water extract resulted in a substantial increase in collagen promotion compared to the Phyllanthus niruri water extract containing the full range of molecular weights. Specifically, collagen promotion provided by the low molecular weight fraction (2.03) was 34% higher compared to that provided by the water extract containing both high and low molecular weight species (1.51).

Moreover, this data shows that the high molecular weight fraction actually inhibits the efficacy of the low molecular weight fraction. The low molecular weight fraction constituted approximately 69.6% by weight (6.4 g) of the total Phyllanthus niruri water extract. The high molecular weight fraction was approximately 30.4% by weight of the total *Phyllanthus niruri* water extract (2.8 g) Accordingly, the expected collagen promotion for the entire water extract would be (0.696×2.03)+(0.304×1.55), or 1.88. However, the actual collagen promotion provided by the unfractionated water extract was 1.51, approximately 20% lower than the expected value. This discrepancy suggests that the high molecular weight fraction inhibits the efficacy of the low molecular weight fraction.

EXAMPLE VI

Topical formulations according to the invention were made using the ingredients shown in Table 5 and Table 6.

TABLE 5

| INCI Name | Trade Name | Percentage |
|---|---|---|
| WATER | PURIFIED WATER | 71.59 |
| Xanthan Gum | Keltrol CG | 0.16 |
| Edetate Disodium | Versene NA | 0.15 |
| White Petrolatum | Perfecta | 5 |
| Medium Chain Triglyceride | Labrafac CC | 0.75 |
| Glycerin | GLYCEROL | 5.50 |
| *Ricinus Communis* Seed Oil | Castor Oil | 1.8 |
| Cetyl Alcohol, NF | Lanette 16 | 2.2 |
| Emulsifying Wax, NF | PolaWax, NF | 1.5 |
| Cocoa Butter | Cocoa Butter, NF | 2 |
| Glyceryl Stearate SE | Glyceryl Stearate SE | 3.00 |
| Glyceryl Stearate/PEG 100 Stearate | Lexemul 561 | 5.00 |
| Diazolidinyl Urea | Germall II | 0.25 |
| Low Molecular Weight Fraction of Water Extract of *Phyllanthus niruri* from Example 1 | | 1.00 |
| Iodopropynyl Butylcarbonate | Glycacil L | 0.1 |

This topical formulation was made as follows.

Water Phase
  Step 1. Purified Water was charged into the main container at a temperature of 20-40° C.
  Step 2. Xanthan Gum NF was added to the main container. A 30 mesh screen may be used if lumpy.
  Step 3. The wall of the main container was rinsed with Purified Water to remove any Xanthan Gum from the walls.
  Step 4. The batch was mixed for 15-25 minutes. Hydration of the gum was checked.
  Step 5. Glycerin USP Special and Edetate Disodium USP were added.
  Step 6. The batch was heated to 65° C. (63-67° C.) while mixing.

Oil Phase
  Step 1. Into a clean suitable phase container, the following chemicals were added in this order: Medium Chain Triglycerides, Castor Oil, Cocoa Butter, and Premelted Petrolatum USP.
  Step 2. The oil phase temperature was set at 65° C. (63-67° C.) and mixing at medium speed was started.
  Step 3. While heating the batch to 65° C., the following chemicals were added in this order, allowing each to dissolve before adding the next: Glyceryl Stearate SE, Cetyl Alcohol, Emulsifying Wax, and Glyceryl Stearate.
  Step 4. When the temperature reached 65° C. (63-67° C.), the ingredients were mixed for 15-25 minutes.

Phasing of the Batch, Main Container
  Step 1. When both phases were homogenous and at a temperature of 63-67° C., the oil phase was transferred to the water phase while mixing the water phase at medium speed.
  Step 2. When transfer was completed, the oil phase tank was rinsed with Purified Water. The rinsings were heated to 63-67° C. and added to the main container.
  Step 3. The batch was mixed for 10-20 minutes.
  Step 4. The batch was cooled to 40° C. (38-42° C.).
  Step 5. When temperature was 48-50° C. the mixing speed was increased to medium-high.
  Step 6. *Phyllanthus niruri* (1% active) was added.
  Step 7. When the temperature was at 44° C. or lower, the Diazolidinyl Urea Premix was added.
  Step 8. Iodopropyl Butylcarbamate was added.
  Step 9. The batch was mixed for 5-10 minutes.

Step 10. If required, the batch was QS'd with Purified Water.

Step 11. Mixing was continued and cooling of the batch to 32-34° C. was begun.

Step 12. When the batch reached 33° C. (32-34° C.), mixing and cooling were ended.

Diazolidinyl Urea (Germall II) Premix

Step 1. Purified water was added into a stainless steel premix tank.

Step 2. Diazolidinyl Urea was added with mixing.

Step 3. The ingredients were mixed for an additional 10-20 minutes to dissolve completely.

Step 4. The premix was held for addition to the batch.

TABLE 6

| INCI Name | Trade Name | Percentage |
|---|---|---|
| Water | Purified Water | 55.79 |
| DISODIUM EDTA | EDTA BD | 0.20 |
| Acrylates C10-30 Alkyl Acrylate | Pemulen TR-1 | 0.25 |
| Potassium Cetyl Phosphate | Amphisol K | 1.00 |
| Sodium Hydroxide | Sodium Hydroxide | 0.52 |
| Phenylbenzimidazole Sulfonic Acid | Eusolex 232 | 2.00 |
| Methylene Bis-Benzotriazolyl Tetramethylbutylphenol | Tinosorb M | 1.00 |
| ETHYLHEXYL SALICYLATE | Neoheliopan OS | 3.00 |
| OCTOCRYLENE | Neoheliopan 303 | 2.00 |
| BENZOPHENONE -3 | Uvinul M40 | 0.50 |
| Ethylhexyl Triazone | Uvinul T 150 | 3.00 |
| AVOBENZONE | Parsol 1789 | 2.00 |
| HOMOSALATE | Neo Heliopan HMS | 5.00 |
| Bis-Ethylhexyloxyphenol Methoxyphenyl Triazine | Tinosorb S | 1.00 |
| DIETHYLHEXYL 2,6-NAPHTHALATE | Corapan TQ | 0.01 |
| C12-15 Alkyl Benzoate | Tegosoft TN | 10.00 |
| Cetyl Alcohol | Lanette C16 98-100 MY | 2.50 |
| Glyceryl Stearate and PEG-100 Stearate | Arlacel 165 FL | 2.40 |
| Ethylhexylglycerin | Sensiva SC 50 | 0.50 |
| BHT | Ionol CP | 0.07 |
| Dimethicone/Vinyl Dimethicone Crosspolymer; Silica | Dow Corning 9701 Cosmetic Powder | 0.50 |
| Dimethicone; Tetra Silane | DC 593 | 1.50 |
| SILICA | Spheron L 1500 | 1.00 |
| Dimethicone | DC 200 350 cps | 2.00 |
| Dimethicone; Dimethiconol | DC1403 | 1.00 |
| Fragrance | Fragrance | 0.08 |
| Low Molecular Weight Fraction of Water Extract of *Phyllanthus niruri*, Inventive Example, Ex. 1 | | 1.00 |
| Methylisothiazolinone; Polyaminopropyl Biguanide | Micrcare MTB | 0.18 |

This topical formulation was prepared as follows:

Water Phase

Step 1. Water was added into main mixing container and mixing was started.

Step 2. EDTA BD was added and mixed until dissolved.

Step 3. Mixing speed was increased and Pemulen TR-1 was added. The ingredients were mixed until fully dispersed (30 min).

Step 4. Eusoulex was premixed with Water; an NaOH solution was added to the water phase.

Step 5. Mixing was continued and Amphisol K was added and mixed for 20 min. Heating to 80° C.-85° C. was begun.

Step 6. The temperature was maintained between 80° C.-85° C. until ready for phasing.

Oil Phase

Step 1. Into a premix container, the following were added one by one and mixed
Neo Heliopan OS
Tegosoft TN
Neo Heliopan 303
Uvinul M40
Parsol 1789
Neo Heliopan HMS
Corapan TQ
Lanette C16 98-100 MY
Arlacel 165 FL
Sensiva SC-50
Ionol CP
Dow Corning 9701 Cosmetic Powder.

Step 2. The mixture was heated to 85° C.-90° C. with continued mixing.

Phasing

Step 1. When both phases were between 80° C.-85° C., the oil phase was added to the water phase under homogenization and homogenized for 10 min.

Step 2. The ingredients were cooled to 70° C.-75° C. and Sodium Hydroxide 10% Solution was added and mixed until uniform.

Step 3. When the temperature was below 75° C., Tinosorb M and Tinosorb S were added and mixed for 10 mins. When the temperature was below 45-50 C, Spheron L-1500, dimethicone, DC 1403, and fragrance were added and mixed until uniform.

Step 4. The ingredients were cooled to a temperature of 35° C.-40° C.

Step 5. Microcare MTB was added and mixed until uniform.

Step 6. *Phyllanthus niruri* (1% active) was added and mixed until uniform.

Step 7. The ingredients were homogenized for 5 minutes.

The topical formulations shown in Tables 5 and 6 were put in 50° C. oven for 1 week and showed primary good stability.

We claim:

1. A method of treating a sign of skin aging, comprising topically applying to skin in need of such treatment a cosmetically effective amount of a topical formulation comprising a cosmetically acceptable topical carrier that is an emulsion and a low molecular weight fraction of *Phyllanthus niruri* substantially free of molecular species having a molecular weight of greater than about 100,000 daltons.

* * * * *